United States Patent [19]

Thurston

[11] Patent Number: 4,508,127

[45] Date of Patent: Apr. 2, 1985

[54] FUEL MASS FLOW MEASUREMENT AND CONTROL SYSTEM

[75] Inventor: John F. Thurston, Mesa, Ariz.

[73] Assignee: The Garrett Corporation, Los Angeles, Calif.

[21] Appl. No.: 480,554

[22] Filed: Mar. 30, 1983

[51] Int. Cl.³ .................... G05D 7/00; G01F 1/90; G01N 9/00
[52] U.S. Cl. .................... 137/8; 73/32 A; 73/861.02; 73/DIG. 8; 137/486; 137/835
[58] Field of Search ............ 73/DIG. 8, 24, 30, 32 A, 73/861.19, 861.02, 861.03; 137/825, 826, 835

[56] References Cited

U.S. PATENT DOCUMENTS

| | | |
|---|---|---|
| 2,923,159 | 2/1960 | Mott . |
| 3,273,377 | 9/1966 | Testerman et al. . |
| 3,373,600 | 3/1968 | Taplin . |
| 3,474,805 | 10/1969 | Swartz ............................. 137/835 X |
| 3,504,691 | 4/1970 | Campagnuolo et al. ........ 137/835 X |
| 3,554,004 | 1/1971 | Rauch et al. . |
| 3,566,900 | 3/1971 | Black ............................. 137/839 X |
| 3,672,388 | 6/1972 | Ringwall et al. . |
| 4,050,304 | 9/1977 | Thomas ........................ 73/861.19 X |
| 4,170,894 | 10/1979 | Zupanick . |
| 4,175,423 | 11/1979 | Braun et al. . |
| 4,199,003 | 4/1980 | Goldsmith . |
| 4,262,523 | 4/1981 | Stansfeld ........................ 73/32 A X |
| 4,328,699 | 5/1982 | Drzewiecki . |

Primary Examiner—Charles A. Ruehl
Attorney, Agent, or Firm—J. Richard Konneker; Albert J. Miller

[57] ABSTRACT

A turbine engine fuel measuring and control system which incorporates a fluidic density sensor which is unaffected by variations in the physical characteristics of the fuel supplied to the engine.

16 Claims, 4 Drawing Figures

FUEL MASS FLOW MEASUREMENT AND CONTROL SYSTEM

BACKGROUND OF THE INVENTION

The present invention relates generally to the measurement of mass flow rate. More particularly the invention provides an inferential fuel mass flow rate measurement and control system in which the density of the fuel is precisely measured by a unique fluidic liquid density sensing device. The fluidic device has a very high degree of accuracy which is unaffected by variation in the temperature, pressure or viscosity of the fuel.

As the fuel economy and performance requirements of modern aircraft jet propulsion engines continue to increase, the need to precisely monitor and control the fuel delivery mass flow rates to their gas generators and augmentors has become far more critical than in the past. Conventionally, two approaches have been taken to the mass flow rate measurement of jet engine fuel delivery. Neither has proven wholly satisfactory.

The first approach has been to "inferentially" measure the fuel's mass flow rate by separately measuring its volumetric flow rate and its density, and then combining (by multiplication) the two measured parameters to provide an indication of mass flow rate. Using this indirect approach, volumetric flow can be measured with acceptable accuracy by any of several conventional flowmeters, including turbine, differential pressure, positive displacement, ultrasonic or fluidic devices. However, conventional methods of measuring the fuel's density in the inferential system inpart heretofore unavoidable inaccuracies to the system.

As an example, perhaps the simplest conventional method of measuring liquid density comprises measuring the temperature of the liquid and then obtaining its density via the temperature-density relationship for the particular liquid. While this method is suitable for a single component liquid, it has proven unsatisfactorily inaccurate in the case of multi-component engine fuel due to unavoidable batch variations in such fuel. Additionally, many advanced propulsion engines are required to be operable on a variety of fuel types—an operating characteristic far beyond the capabilities of conventional temperature-density sensing apparatus.

More complex methods of liquid density determination include electrically driven vibrating beam densitometers and devices which measure the dielectric constant of a liquid, the dielectric constant being related to the liquid's density. Inherent in both of these devices, however, are rather poor accuracy and slow frequency response.

The second conventional approach to determining the mass flow rate of a liquid is to measure it directly by utilizing a "true" mass flowmeter. The most widely used device of this type, the angular momentum mass flowmeter, uses a motor-driven or fuel-driven impeller which imparts angular momentum to the fuel at a rate of proportional to the fuel's mass flow rate. The fuel is then flowed through an identically configured turbine which is rotationally restrained by a spring. By electronically measuring the angular deflection of the turbine the mass flow rate of the fuel is directly obtained.

Such conventional true mass flowmeters afford the advantage of being substantially unaffected by variations in the fuel's physical characteristics such as temperature, pressure and viscosity. Thus, a single such mass flowmeter has the potential for accurately measuring the mass flow rate of a variety of engine fuel mixtures. However, the requisite degree of measurement accuracy needed for high technology turbine engines may be achieved only by very precisely manufacturing both the impeller and turbine elements—a very costly process. Additionally, this type of flowmeter has demonstrated the requisite accuracy only within the "cruise" range of the typical turbine propulsion engine. Outside of this range the flowmeter's accuracy falls off markedly.

It can be seen from the foregoing that a need exists for a fuel mass flow rate measuring and control system which eliminates or minimizes above-mentioned and other problems associated with conventional apparatus. Accordingly, it is an object of the present invention to provide such a system.

SUMMARY OF THE INVENTION

The present invention provides an inferential fuel mass flow rate measuring and control system which separately measures the volumetric flow rate and the density of fuel being supplied to a gas turbine aircraft propulsion engine. The sensed volumetric flow rate and density values are automatically multiplied to generate a signal indicative of the fuel mass flow rate. This signal is transmitted to the engine's fuel control computer which responsively controls the actual mass flow rate of fuel to the engine in accordance with a desired supply flow rate.

According to an important aspect of the invention the density-sensing portion of the system comprises fluidic oscillator means which receive and are powered by a portion of the fuel supplied to the engine to create in the oscillator means pulsating pressure signals whose frequencies are indicative of the density of the received fuel. Associated with the oscillator means are pressure control means which function to automatically maintain the fuel's pressure drop across the oscillator means' internal power nozzle at an essentially constant level.

By regulating the jet pressure drop in this manner a unique and quite desirable result is achieved—the density sensing portion of the system, and thus the entire system, is rendered essentially totally insensitive to variations in the physical properties of the fuel. This allows the system, unlike conventional inferential systems, to maintain a high degree of accuracy regardless of variations in the temperature, pressure or viscosity of a particular fuel, fuel batch variations, or changes in the type of fuel actually used.

Since the density sensing portion of the system employs fluidic apparatus, the high degree of measurement accuracy of the system is achieved with considerably less manufacturing expense than in the case of conventional true mass flowmeter systems. Moreover, the inherent simplicity and ruggedness of fluidic control apparatus considerably enhances the reliability of the system.

In a preferred embodiment of the mass flow rate measuring and control system, the fluidic oscillator means are provided with a duality of pressure-to-electric transducer means which convert the oscillator means' pulsating pressure outputs to an oscillating electrical signal having a frequency indicative of the sensed fuel density. In a conventional manner the transducer means are connected to the oscillator means in a mutually opposite polarity relationship to thereby substantially eliminate output signal error caused by any mechanical vibration to which the oscillator means may be subjected during operation of the system.

DETAILED DESCRIPTION

Figure 1:
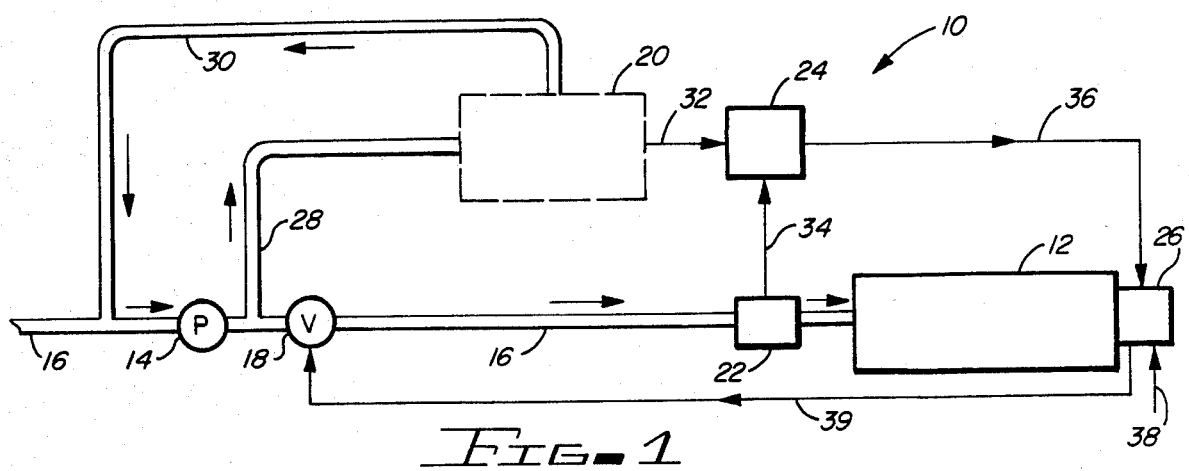
FIG. 1 is a schematic diagram of an inferential fuel mass flow rate measuring and control system embodying principles of the present invention.

Schematically illustrated in FIG. 1 is an inferential fuel mass flow rate measuring and control system 10 which embodies principles of the present invention and is utilized in conjunction with a gas turbine aircraft propulsion engine 12. During engine operation fuel from a source thereof (not shown) is supplied to the engine by a pump 14, via a main supply conduit 16, through a throttling valve 18.

The system 10 comprises a fuel density sensing portion 20, a volumetric flow sensing portion in the form of a conventional turbine flowmeter 22 positioned in conduit 16 between the engine 12 and valve 18, an electronic signal processor 24, and a fuel control computer 26 operatively associated with the engine 12. In a manner subsequently described, the density sensor 20 receives and is powered by a small flow of fuel supplied thereto by branch supply conduit 28 connected to the main conduit 16 between the pump 14 and the valve 18. Fuel supplied to density sensor 20 is returned to the main conduit 16 upstream of pump 14 by a small return conduit 30.

During operation of the system 10, the density sensor 20 generates an electrical output signal 32 indicative of the density of the fuel received by engine 12, while the flowmeter 22 generates an electrical output signal 34 indicative of the volumetric flow of fuel to the engine 12. The signal processor 24 receives the density and volumetric flow output signals 32,34, automatically multiplies the two signals, and responsively transmits to the fuel control computer 26 an input signal 36 which is precisely indicative of the actual mass flow rate of fuel received by engine 12 via the main supply conduit 16. In a conventional manner the fuel control computer 26 compares the value of mass flow rate signal 36 to a control input signal 38 representing a desired fuel mass inflow rate and responsively makes any necessary adjustments to the engine fuel inflow by automatically adjusting the throttling valve 18 by means of a valve positioning signal 39 generated by the computer.

Unlike conventional inferential mass flow measuring systems, the system 10 is essentially completely insensitive to variations in the physical characteristics of the fuel being supplied to engine 12. More specifically, despite variations in the temperature, pressure or viscosity of a particular fuel being used, or variations in the type of fuel used, the high degree of accuracy of the mass flow signal 36, and thus of the entire system 10, is maintained. This highly desirable feature of the system is achieved by virtue of the unique structure and operation of the fluid density sensor 20 which will now be described with reference to FIG. 2.

Figure 2:
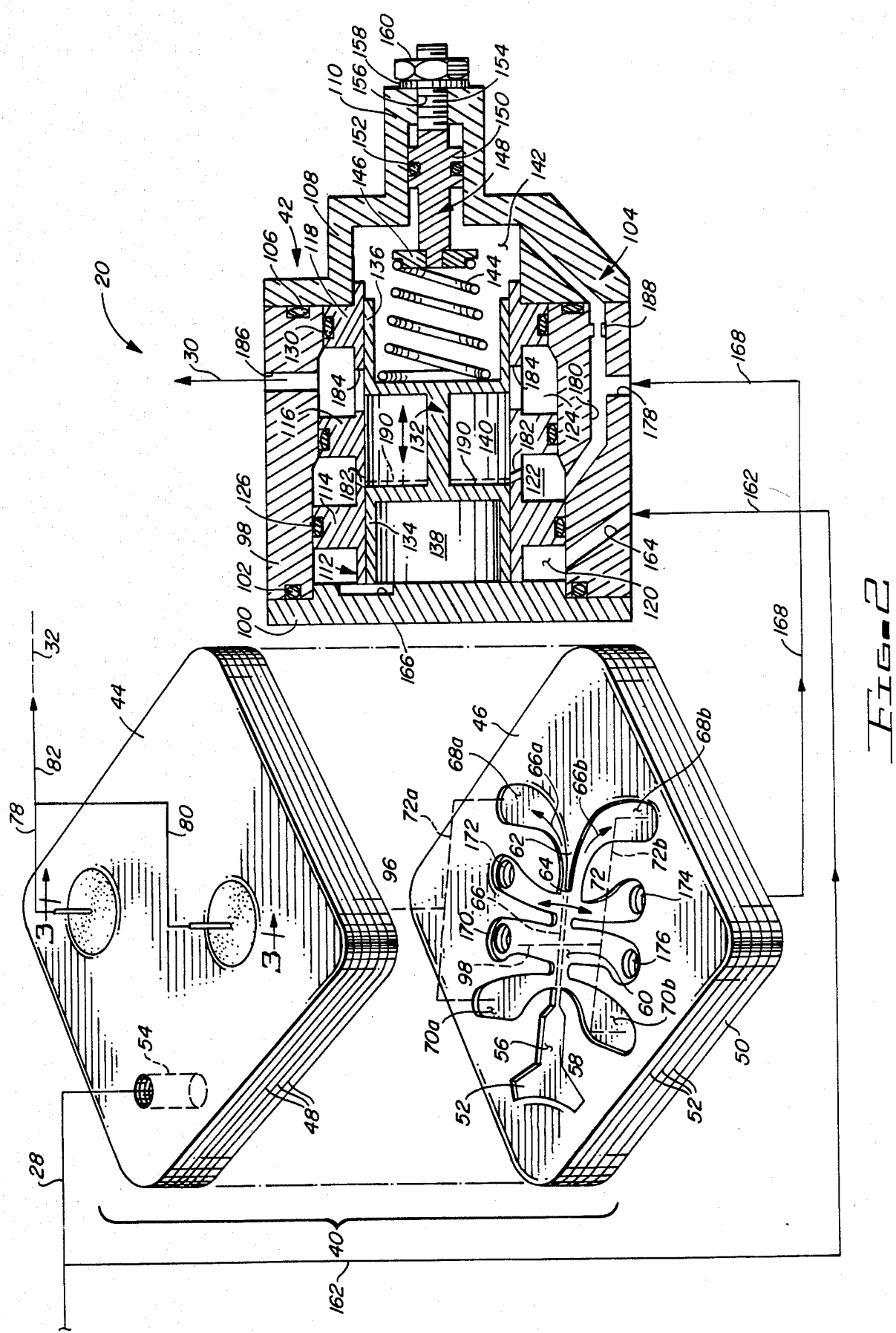
FIG. 2 is an enlarged view, partially in exploded perspective and partially in cross-section, of the system's density sensing portion, such portion including a fluidic oscillator and an associated pressure regulator.

As illustrated in FIG. 2, the density sensor 20 comprises two operatively associated components—a fluidic oscillator 40 and a fluid pressure regulator 42. The fluidic oscillator 40 is of a generally conventional laminated construction, having a monolithic body consisting of a multiplicity of thin, rectangular metal laminae mutually bonded together in an edge-aligned relationship. In the depicted oscillator such laminae comprise an upper end lamina 44, a central or main lamina 46, a series of upper auxiliary laminae 48 positioned between laminae 44 and 46, a lower end lamina 50, and a series of lower auxiliary laminae 52 positioned between laminae 46 and 50.

The auxiliary laminae each have suitable openings formed therein (not all of which are illustrated in FIG. 2) which, in a conventional manner, collectively define various internal passages within the oscillator body leading to and from the main lamina 46. One such passage is a supply passage 54 which extends downwardly through upper end lamina 44 and each of the auxiliary laminae 48 adjacent the left corner of the oscillator body.

The lower end opening of supply passage 54 is positioned directly above a supply channel 56 formed in the main lamina 46 and extending lengthwise toward the right corner of the oscillator body. At its right end the supply channel is necked down to form a power nozzle 58 which opens at its discharge end into the left end of an elongated interaction channel 60 also formed through main lamina 46. The right or downstream end of the interaction channel is laterally divided by an elongated splitter portion 62 of main lamina 46 having a leading edge 64. Leading edge 64 faces and is laterally aligned with the outlet of the power nozzle 58.

During operation of the fuel mass flow rate measuring and control system 10, a small quantity of fuel is continuously supplied to the supply channel 56 through the supply opening 54 to which the branch supply conduit 28 is connected. The fuel received in supply channel 56 is forced outwardly through power nozzle 58 to thereby form a fuel jet 66 which longitudinally traverses the interaction channel 60 and impinges upon the leading splitter edge 64. Splitter edge 64 divides the jet 66 into two substreams 66a, 66b, which respectively flow along opposite sides of splitter 62 into a pair of main lamina receiving channels 68a, 68b extending laterally outwardly of splitter 62, on opposite sides thereof, downstream from the leading splitter edge 64.

At the power nozzle end of the interaction channel 60 are a pair of jet-control channels 70a, 70b which communicate at their inner ends with the interaction channel directly adjacent the outlet of power nozzle 58 and extend laterally outwardly from the interaction channel in opposite directions. The outer ends of channels 68a and 70a communicate through a feedback passage 72a, and the outer ends of channels 68b and 70b communicate through a feedback passage 72b. While schematically illustrated by the dashed lines directly above main lamina 46 for the sake of clarity, these feedback passages are actually positioned in the upper portion of the oscillator body, being collectively defined by various cooperating channels and passages formed through the upper auxiliary laminae 48 (similarly to the laminae openings which define inlet passage 54).

When the fuel jet 66 first impinges upon splitter edge 64, one or the other of the substreams 66a, 66b is initially at least minutely larger in cross-section than the other substream. This initial unequal division of the fuel jet creates a relative pressure differential between the receiving channels 68a, 68b. For example, if substream 66a is initially larger in cross-section than substream 66b the fluid pressure in receiving channel 68a is lightly larger than the corresponding pressure in receiving channel 68b. This pressure differential between the receiving channels 68a, 68b is imposed upon the jet-control channels 70a, 70b via the feedback channels 72a, 72b, respectively, with the fluid pressure in channel 70a being initially greater than that in channel 70b. The fluid pressure imbalance between channels 70a, 70b (which communicate at their inner ends with interaction channel 60 on opposite sides of the fuel jet 66) causes the jet 66 to pivot slightly in a clockwise direction (as viewed in FIG. 2) relative to the splitter edge 64.

Such pivoting of the fuel jet increases the cross-sectional area of substream 66b relative to that of substream 66a thereby reversing the pressure differential between receiving channels 68a, 68b. This reversal, via feedback channels 72a, 72b, reverses the pressure differential between channels 70a, 70b, causing a counterclockwise pivoting of the fuel jet, again reversing the pressure differential between receiving channels 68a, 68b.

The above-described pressure reversal cycle causes the fuel jet 66 to continuously and very rapidly oscillate from side to side as indicated by the double-ended arrow 72 in FIG. 2. In turn, such jet oscillation creates fluid pressure pulsations in each of the feedback channels 72a, 72b. Importantly, the frequency of such oscillations is very precisely indicative of the density of the fuel ultimately supplied to the engine 12.

By means of a pair of disc-shaped piezoelectric transducers 74,76 (FIG. 3) the density-indicative pressure pulsations in feedback channels 72a, 72b are converted to oscillating electrical signals which are transmitted through output leads 78,80 respectively associated with transducers 74,76. Leads 78,80 are coupled to a common output lead 82 through which the density sensor output signal 32 is transmitted to the electronic signal processor 24 (FIG. 1).

Figure 3:
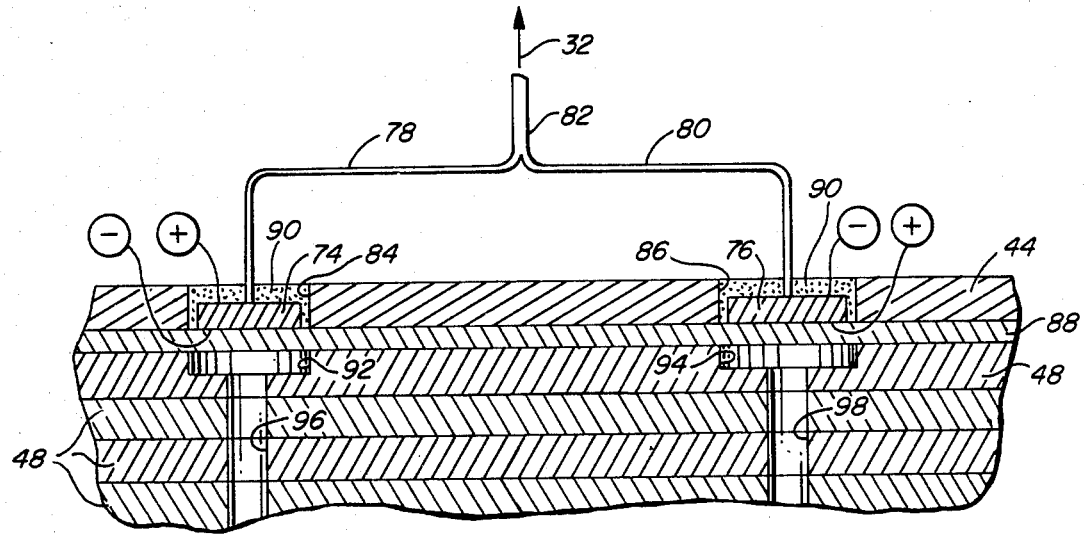
FIG. 3 is an enlarged cross-sectional view taken through the oscillator along line 3—3 and illustrating a pair of pressure-to-electric transducers operatively connected to the oscillator.

As can best be seen in FIG. 3, transducers 74,76 are respectively recessed within slightly larger diameter circular openings 84,86 formed through the upper density sensor lamina 44. The bottom end of each transducer rests upon a thin metal diaphragm plate 88 sandwiched between the upper lamina 44 and the uppermost auxiliary lamina 48. A conventional potting compound 90 is used to secure and seal the transducers within the lamina openings 84,86. Directly beneath the diaphragm 88 are circular recesses which are formed in the uppermost auxiliary lamina 48, such recesses being respectively aligned with and generally of the same diameter as the transducer openings 84,86. Recesses 92,94 respectively communicate with the internal feedback passages 72a, 72b via vertically extending pressure transmission passages 96,98 (see also FIG. 2) defined within the upper auxiliary laminae 48.

The fluid pressure pulses alternately created in the feedback passages are transmitted to the recess 92,94 by the vertical passages 96,98 to thereby cause the alternate outward (i.e., upward in FIG. 3) flexure of the diaphragm portions circumscribed by openings 84,86 and the transducers associated therewith. Transducers 74,76 are bonded to the diaphragm 88 (with a conventional conductive epoxy cement) in a mutually opposite polarity relationship, with the negative end of transucer 74 and the positive end of transducer 76 abutting the diaphragm.

Figure 4:
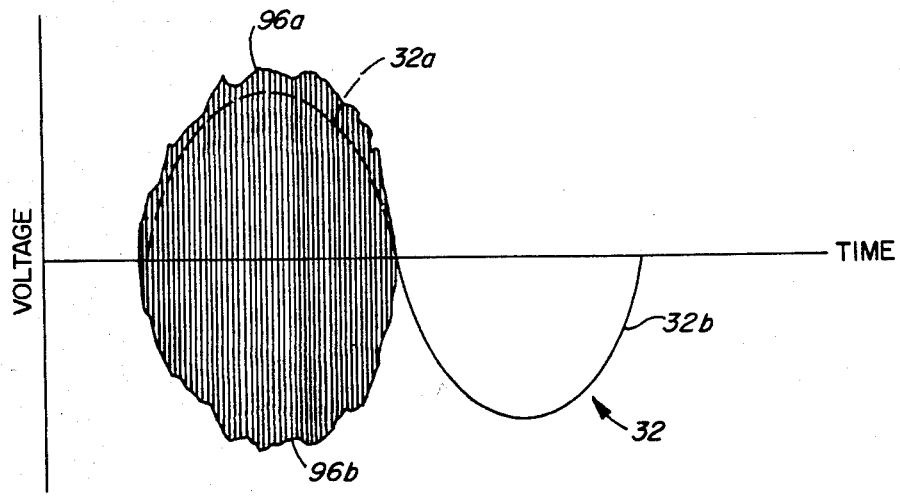
FIG. 4 is a graph which illustrates the manner in which the transducers cooperate to substantially eliminate vibrationally induced error in the oscillator's output signal.

This opposite polarity transducer connection causes the density sensor output signal 32 to assume the sinusoidal configuration indicated in FIG. 4—the positive half 32a of the sine wave being attributable to transducer 74, and the negative half 32b being attributable to transducer 76. Such opposite polarity connection of the transducers also renders the density sensor substantially totally insensitive to mechanical vibration in the following manner.

If the density sensor experiences mechanical vibration, the diaphragm portions beneath lamina openings 84,86 will be subjected to oscillating vertical flexure (as viewed in FIG. 3) such that at the same instant each transucer will be flexed either upwardly or downwardly. Upward vibrational flexure (for example) of transucer 74 adds a false signal or vibrational "noise" 96a to is portion 32a of output signal 32. However, the concomitant upward vibrational flexure of transducer 76 produces in the common lead 82 an identically configured false signal 96b which is of opposite polarity relative to noise signal 96a, thereby cancelling it out completely and leaving the transducer output signal portion 32a (or signal portion 32b as the case may be) undistorted by vibrational noise.

As mentioned previously, the density sensing portion 20 (FIG. 1) of system 10 is uniquely unaffected by variations in the physical characteristics of the fuel being supplied to the engine 12 via conduit 16. More specifically, in the present invention the density-indicative output signal 32 retains its high degree of accuracy despite variations in the temperature, pressure and/or viscosity of the supplied fuel.

To accomplish this novel result the pressure regulator 42 (FIG. 2) is utilized, in a manner subsequently described, to automatically maintain the fuel pressure drop across the oscillator power nozzle 58 at a predetermined, essentially constant level. The efficacy of such pressure drop regulation may be demonstrated by an examination of the general relationship among several operating characteristics of the oscillator. First, the relationship between the fuel density D, pressure drop $\Delta P$ across the power nozzle 58, and the power nozzle exit velocity V is expressed by the equation:

$$D = 2\Delta P/V^2$$

Since, as is well known in the fluidics art, the frequency F of the feedback channel pressure pulses (and thus the frequency of the ouput signal 32) is proportional to the power nozzle outlet velocity V, the above equation may be rewritten as follows, with k being the proportionality constant:

$$D = 2\Delta P/(kF)^2$$

By maintaining the nozzle pressure drop $\Delta P$ constant it can be seen that the relationship between the fuel density D and the output signal frequency F becomes:

$$D = C_1/F^2,$$

$C_1$ being the overall calibration constant of the fluidic oscillator 40. Because of this proportionality achieved between the fuel density and oscillator frequency by the pressure regulator 42, potential inaccuracy in output signal 32 caused by variances in the fuel's temperature, pressure or viscosity (or caused by the use of a different fuel) is substantially completely eliminated.

Referring again to FIG. 2, the pressure regulator 42 has a hollow, open-ended, cylindrical body 98. At the left end of body 98 an end cap 100 is secured (by means not illustrated in FIG. 2), a seal between the body and cap 98,100 being provided by an O-ring 102 positioned therebetween. At the right end of the regulator body an end cap 104 is similarly secured and sealed with an O-ring 106. A hollow central portion 108 of cap 104 projects axially outwardly from the remainder of the cap and, in turn, has a hollow, outwardly projecting central stem portion 110.

Coaxially disposed within body 98, and bearing at its opposite ends against caps 100,104 is a hollow, open-ended cylindrical liner 112. From left to right along its length the liner has three mutually spaced annular flanges 114,116,118 which bear against the inner surface of regulator body 98. These flanges define between the liner 112 and the body 98, from left to right, three mutually spaced annular chambers 120,122,124 within the regulator. Sealing between these flanges and the regulator body is provided by O-rings 126,128,30 respectively carried by the flanges 114,116,118.

An open-ended spool valve member 132 having mutually spaced opposite end portion 134,136 is slidably received within the liner 112 for axial movement relative thereto. Valve member 132 defines with the regulator liner and end caps, from left to right within the regulator, a chamber 138 adjacent end cap 100, an annular chamber 140 between the valve end portions 134,136, and a chamber 142 adjacent end cap 104.

Valve member 132 is biased leftwardly toward engagement with end cap 100 by means of a frustroconically shaped compression spring 144 positioned within chamber 142 and extending axially into the open valve end portion 136. Spring 144 bears at its base end against the rightwardly facing inner end surface of valve end portion 136, with the opposite end of the spring being seated on a grooved flange 146 carried on the inner end of an adjusting bolt 148. Bolt 148 extends outwardly through the cap stem 110, and slidably engages the interior surface thereof by means of annularly flanged central portion 150 of the bolt upon which is mounted an appropriate O-ring seal 152. A threaded outer end portion 154 of the bolt is received in a threaded opening 156 formed through the outer end of stem 110 with the outer end of the bolt projecting rightwardly of the stem. This construction permits the biasing force of spring 144 to be adjusted simply by tightening or loosening the bolt 148. After adjustment of such biasing force in this manner, the bolt may be locked into position by means of a lock washer 158 and nut 160 on its outer end.

The pressure regulator 42 functions to regulate the pressure drop across the oscillator power nozzle 58 by receiving and utilizing two fuel pressure signals—the first signal being indicative of the fuel pressure upstream from the nozzle, and the second signal being indicative of the fuel jet pressure downstream from the nozzle.

The first signal is transmitted to the regulator via a branch conduit 162 (FIG. 2) interconnected between fuel supply conduit 28, just upstream of oscillator inlet 54, and an inlet passage 164 formed in the regulator body 98. Inlet 164 opens into the annular regulator chamber 120 which communicates with the valve chamber 138 via a recess 166 formed in the inner surface of the end cap 100. Fuel entering regulator inlet 164 is forced via chamber 120 and recess 166 into the valve chamber 138 where it exerts a rightward force on valve 132 which is resisted by the preset biasing force of spring 144.

The second fuel pressure indicative signal is transmitted to the regulator through an outlet conduit 168 interconnected between the oscillator 40 and the regulator. All of the fuel supplied to the oscillator through its inlet 54 is ultimately forced into conduit 168 via vent passages 170,172,174,176 formed in the main oscillator lamina 46 and extending laterally from the interaction channel 60 between the jet-control channels 70a,70b and the receiving channels 68a,68b. At their outer ends these vent passages are extended downwardly into the lower auxiliary laminae 52 where they are interconnected into an oscillator outlet passage (not shown in FIG. 2), the outlet passage in turn being connected to the upstream end of conduit 168. The downstream end of conduit 168 is connected to an inlet 178 formed in the regulator body. Inlet 178 communicates with an inlet passage 180 which extends between the annular chamber 122 and the regulator chamber 142.

The pressure of the fuel entering inlet 178 is indicative of the discharge pressure of the oscillator power nozzle 58. A portion of the fuel entering inlet 178 flows leftwardly through passage 180 into the annular chamber 120 and then into the annular chamber 140 through a series of small metering ports 182 extending through the liner 112. From chamber 140 the fuel flows outwardly through a series of transfer ports 184 formed through liner 112 and into the annular chamber 124. It then flows outwardly through a regulator outlet passage 186 to which is connected the fuel return conduit 30. There is thus a continuous flow of fuel sequentially through the supply conduit 28, the oscillator 40, the conduit 168, the regulator 42 and the return conduit 30 back to the main supply conduit 16 (FIG. 1).

When the system 10 is initially started up a portion of the fuel entering regulator inlet 178 (FIG. 2) is also forced rightwardly through passage 180, across an orifice 188, and into the regulator chamber 142 wherein the fuel is trapped and exerts a leftward pressure force upon the valve 132. This force is supplemented by the force of spring 144 and opposed by the pressure force of the fuel within chamber 138 (the pressure in chamber 138 being, of course, higher than the pressure in chamber 142). The spring force is pre-adjusted (with bolt 148) so that when the pressure drop across nozzle 58 is at its setpoint level the valve 132 is moved slightly rightwardly from its "at rest" position indicated in solid lines in FIG. 2. More specifically the valve member is forced rightwardly to a normal operating position in which the back end surface 190 of valve end 134 is moved across a portion of the metering orifices 182 (as indicated by the dashed line 190). In this position valve end 134 partially blocks such orifices, thereby restricting the flow of fuel therethrough.

If, because of a change in the temperature, pressure or viscosity of the fuel, the pressure drop across nozzle 58 deviates from its set point value the existing pressure differential between the fuel in conduits 162,168 is correspondingly altered.

As a result, valve member 132 will be automatically moved to increase or decrease its restriction of the metering ports 182 thereby changing the pressure differential between conduits 162,168 and bringing the nozzle pressure drop back to its predetermined setpoint level.

To illustrate the pressure regulator's operational control function, let it be assumed that the pressure in supply conduit 28 increases, thereby increasing the power nozzle pressure drop above its setpoint level. Via conduit 162 the pressure in regulator chamber 138 will correspondingly increase, thereby moving the dashed line valve surface 190 slightly rightwardly to further restrict the metering ports 182. This further port restriction elevates the flow resistance through the regulator (i.e., from conduit 168 to return conduit 30), thus increasing the pressure within conduit 168 (and thus the internal oscillator pressure downstream from power nozzle 58) to return the nozzle pressure drop to the correct level. In a similar manner, if the pressure in conduit 28 drops, the valve member 132 is moved slightly to the left, thereby further opening the metering orifices 182 and lowering the pressure in conduit 168.

It can be seen from the foregoing that, due to the unique density sensing apparatus 20 just described, the present invention provides an inferential fuel measuring and control system which eliminates or minimizes the inaccuracies present in conventional inferential systems. Importantly, this very desirable result is achieved without the relatively high costs typically associates with the "direct" measuring systems previously described.

The foregoing detailed description is to be clearly understood as given by way of illustration and example only, the spirit and scope of this invention being limited solely by the appended claims.

What is claimed is:

1. Apparatus for accurately measuring the density of a flowing fluid comprising:
    (a) fluidic oscillator means having:
        (1) power nozzle means for receiving a flow of fluid and converting the received fluid to a fluid jet, and
        (2) means for utilizing the jet to create a pulsating pressure signal having a frequency indicative of the density of the received fluid; and
    (b) means for maintaining the pressure drop across said power nozzle means essentially constant despite variations in the pressure of fluid received by said power nozzle means, whereby the frequency of said pulsating pressure signal is rendered substantially independent of the temperature, pressure and viscosity of the received fluid.

2. The apparatus of claim 1 wherein said oscillator means have an inlet and an outlet; said apparatus further comprises supply conduit means for flowing a pressurized fluid from a source thereof into said oscillator means inlet; and said means (b) comprise a differential pressure regulator having first and second inlets, first conduit means interconnected between said supply conduit means and said first regulator inlet, and second conduit means interconnected between said oscillator means outlet and said second regulator inlet.

3. The apparatus of claim 2 wherein said pressure regulator has an outlet, a flow passage communicating with said regulator outlet and said second regulator inlet, and valve means positioned in said flow passage for variably restricting said flow passage in response to variations in fluid pressure differential between fluid in said first and second conduit means.

4. The apparatus of claim 1 further comprising transducer means for converting said pulsating pressure signal to a pulsating electrical signal having a frequency indicative of the density of the received fluid.

5. The apparatus of claim 4 wherein said means (a)(2) include means for utilizing the jet to create a second pulsating pressure signal having a frequency indicative of the density of the received fluid; wherein said transducer means include a duality of pressure-to-electric transducers each adapted to generate a pulsating electrical output signal having a frequency corresponding to the frequency of a different one of said pulsating pressure signals; and wherein said apparatus further comprises means for utilizing said pulsating electrical signals to generate a composite oscillating electrical output signal having a frequency indicative of the density of the received fluid.

6. The apparatus of claim 5 further comprising means for rendering the frequency of said oscillating electrical output signal substantially insensitive to mechanical vibration imposed upon said transducers.

7. The apparatus of claim 6 wherein said transducers are piezoelectric transducers and wherein said last-mentioned means include means for mounting said transducers on said oscillator means in a mutually opposite polarity relationship.

8. Apparatus for precisely monitoring the mass flow rate of a liquid flowing through a supply conduit or the like, comprising:
    (a) means for receiving at least a portion of the fluid flow through the supply conduit and responsively generating a variable first output signal indicative of the density of the flowing fluid;
    (b) means, operatively connected to said means (a), for rendering the magnitude of said first output signal substantially insensitive to variations in the physical characteristics of the of the flowing fluid;
    (c) means for sensing the volumetric liquid flow rate through the supply conduit and responsively generating a second output signal indicative of such volumetric flow rate; and
    (d) means for receiving said first and second output signals and responsively generating a third output signal indicative of the liquid mass flow rate through the supply conduit, said means (a) including a fluidic oscillator having a power nozzle positioned to receive and discharge the received fluid, and said means (b) including pressure regulating means for regulating the pressure drop across said power nozzle.

9. The apparatus of claim 8 wherein said fluidic oscillator has an inlet and an outlet, and said pressure regulator means comprise a differential pressure regulator having a first inlet in fluid communication with said oscillator inlet, and a second inlet in fluid communication with said oscillator outlet.

10. The apparatus of claim 9 wherein said means (c) comprise a volumetric flow meter adapted for operative connection to the supply conduit.

11. Vibration insensitive liquid density sensing apparatus comprising:
    (a) fluidic oscillator means having first and second internal feedback passages, power nozzle means for receiving liquid from a source thereof and converting the received liquid to a liquid jet, means for utilizing the jet to create in said feedback passages pressure pulsations having frequencies each indicative of the density of the received liquid, and first and second pressure transmission passages respectively communicating with said first and second feedback passages;

(b) first diaphragm means extending across said first pressure transmission passage for outward flexure in response to pressure pulsations in said first pressure transmission passage;

(c) second diaphragm means extending across said second pressure transmission passage for outward flexure in response to pressure pulsations in said second pressure transmission passage;

(d) first transducer means secured to said first diaphragm means for generating a positive output signal in response to outward flexure of said first diaphragm means;

(e) second transducer means secured to said second diaphragm means for generating a negative output signal in response to outward flexure of said second diaphragm means;

(f) means for utilizing both of said positive and negative output signals to create a composite oscillating output signal having a frequency indicative of the frequencies of said pressure pulsations in said first and second feedback passages; and (g) means for regulating the pressure drop across said power nozzle means to thereby render the frequency of said composite output signal substantially totally independent of the physical characteristics of the received liquid.

12. The apparatus of claim 11 wherein said oscillator means have an inlet passage and an outlet passage, said inlet and outlet passages respectively communicating with the inlet and outlet of said power nozzle means; wherein said regulating means include a differential pressure regulator having first and second inlets; and wherein said apparatus further comprises conduit means communicating said oscillator means inlet passage with said first pressure regulator inlet, and conduit means communicating said oscillator means outlet passage with said second inlet of said pressure regulator.

13. The apparatus of claim 11 wherein each of said first and second transducer means comprise a piezoelectric transducer, said piezoelectric transducers being secured to their respective diaphragm means in a mutually opposite polarity relationship.

14. A system for supplying a predetermined, precisely controlled mass flow of fuel to an engine comprising:

(a) first conduit means interconnectable between the engine and a fuel source;

(b) pump means operatively disposed along said first conduit means for flowing fuel therethrough to the engine;

(c) fluidic oscillator means having:
  (1) an inlet,
  (2) an outlet,
  (3) an internal flow path opening outwardly through said inlet and outlet,
  (4) a power nozzle operatively disposed along said flow path for creating therein a jet from fuel traversing said nozzle, and
  (5) means for utilizing the jet to generate a first output signal in response to fuel flow through said flow path and across said nozzle, said first output signal being indicative of the density of fuel flowing through said oscillator means;

(d) second conduit means, interconnected between said first conduit means, downstream from said pump means, and said oscillator means inlet, for flowing fuel into and through said oscillator means;

(e) pressure regulator means for maintaining the fuel pressure drop across said power nozzle at a predetermined, essentially constant level, said pressure regulator means having:
  (1) a first inlet,
  (2) a second inlet,
  (3) an outlet,
  (4) an internal flow passage opening outwardly through said outlet and second inlet of said regulator means, and
  (5) valve means positioned in said regulator means flow passage for variably restricting the same in response to a variance between first and second pressure signals received by said pressure regulator means;

(f) third conduit means, interconnected between said second conduit means and said first inlet of said pressure regulator means, for transmitting said first pressure signal to said pressure regulator means;

(g) fourth conduit means, interconnected between said oscillator means outlet and said second pressure regulator means inlet, for transmitting said second pressure signal to said pressure regulator means and for flowing fuel discharged from said oscillator means into and through said flow passage of said pressure regulator means;

(h) fifth conduit means, interconnected between said first conduit means and said pressure regulator means outlet, for returning to said first conduit means fuel discharged from said flow passage of said pressure regulator means;

(i) means for sensing the volumetric fuel flow rate through said first conduit means and responsively generating a second output signal indicative of such volumetric fuel flow rate;

(j) signal processing means for receiving said first and second output signals and responsively generating a third output signal indicative of the mass fuel flow rate through said first conduit means; and (k) fuel supply control means for receiving said third output signal and responsively adjusting the mass flow rate of fuel received by the engine through said first conduit means to thereby maintain such mass flow rate at a predetermined level.

15. A method of regulating the mass flow rate of fuel received by an engine through supply conduit means or the like, said method comprising the steps of:

(a) providing fluidic oscillator means for receiving a flow of fuel therethrough and responsively generating a first output signal indicative of the density of such fuel;

(b) providing a pressure regulator having a first inlet, a second inlet, an outlet, and an internal flow passage interconnecting said outlet and said second inlet, said pressure regulator being adapted to maintain a predetermined pressure differential between first and second fluid pressures respectively transmitted to its first and second inlets;

(c) communicating the interior of the supply conduit means with said first inlet of said pressure regulator;

(d) flowing fuel from the supply conduit means sequentially through said oscillator means, into said second pressure regulator inlet and through said pressure regulator flow passage, and from said pressure regulator outlet back to the supply conduit means;

(e) generating a second output signal indicative of the volumetric rate of fuel flow through the supply conduit means; and (f) simultaneously utilizing said first and second output signals to regulate the mass flow rate of fuel received by the engine through the supply conduit means.

16. The method of claim 15 wherein said step (e) includes operatively positioning a volumetric flow meter along the supply conduit means, said flow meter being adapted to generate said second output signal, and wherein said step (f) includes the steps of transmitting said first and second output signals to a signal processor adapted to responsively generate a third output signal indicative of the product of said first and second output signals.

* * * * *